United States Patent
Fosodeder et al.

(10) Patent No.: US 11,109,842 B2
(45) Date of Patent: Sep. 7, 2021

(54) METHOD AND SYSTEM FOR ENHANCED VISUALIZATION OF INDIVIDUAL IMAGES IN A REAL-TIME SCAN

(71) Applicant: General Electric Company, Schenectady, NY (US)

(72) Inventors: Erwin Fosodeder, Zipf (AT); Helmut Brandl, Zipf (AT); David Puehringer, Zipf (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1033 days.

(21) Appl. No.: 14/565,675

(22) Filed: Dec. 10, 2014

(65) Prior Publication Data

US 2016/0173770 A1 Jun. 16, 2016

(51) Int. Cl.
*A61B 8/08* (2006.01)
*G01S 7/52* (2006.01)

(52) U.S. Cl.
CPC ........ *A61B 8/5207* (2013.01); *G01S 7/52098* (2013.01); *G01S 7/52047* (2013.01)

(58) Field of Classification Search
CPC ............ G01S 7/52098; G01S 7/52047; A61B 8/5207
USPC ...................................................... 348/163
See application file for complete search history.

(56) References Cited

U.S. PATENT DOCUMENTS 6,056,691 A 5/2000 Urbano et al.
6,673,017 B1 1/2004 Jackson 2005/0228280 A1* 10/2005 Ustuner ............... A61B 8/06
600/443
2008/0298654 A1* 12/2008 Roth ................. A61B 8/12
382/128
2010/0195881 A1* 8/2010 Orderud .............. A61B 8/08
382/131

FOREIGN PATENT DOCUMENTS

CN  101496061 A  7/2009
CN  101901335 A  12/2010
JP  2009540911 A  11/2009

OTHER PUBLICATIONS

International Search Report and Written Opinion from Corresponding PCT application No. PCT/2015/063433 dated Mar. 14, 2016; 13 pages.
Office Action from related Chinese Patent Application No. 201580067331.X, dated Jun. 3, 2019, 12 pages.

* cited by examiner

*Primary Examiner* — Kate H Luo
*Assistant Examiner* — Kristin Dobbs
(74) *Attorney, Agent, or Firm* — McAndrews, Held & Malloy, Ltd.; Jacob Groethe; David Bates

(57) ABSTRACT

Various embodiments include a system and method that enhance the visualization of selected individual images from a real-time scan. The method can include acquiring ultrasound image data at an ultrasound system. The method may include processing the acquired ultrasound image data according to cine sequence processing parameters to generate a cine sequence. The cine sequence includes a plurality of frames, each of the frames having a first resolution. The method can include receiving a trigger. The method may include processing the acquired ultrasound image data according to still image processing parameters in response to the trigger to generate a still image. The still image has a second resolution that is higher than the first resolution.

13 Claims, 4 Drawing Sheets

METHOD AND SYSTEM FOR ENHANCED VISUALIZATION OF INDIVIDUAL IMAGES IN A REAL-TIME SCAN

CROSS-REFERENCE TO RELATED APPLICATIONS/INCORPORATION BY REFERENCE

[Not Applicable]

FIELD OF THE INVENTION

Certain embodiments of the invention relate to ultrasound imaging. More specifically, certain embodiments of the invention relate to a method and system for enhancing the visualization of selected individual images from a real-time cine sequence.

BACKGROUND OF THE INVENTION

Ultrasound imaging is a medical imaging technique for imaging organs and soft tissues in a human body. Ultrasound imaging uses non-invasive high frequency sound waves to produce images, which may be viewed as static or real-time motion two-dimensional (2D) images, static three-dimensional (3D) images, and/or four-dimensional (4D) images (i.e., 3D real-time motion images).

Sonographers typically operate an ultrasound machine to acquire a real-time scan. The acquired ultrasound data is processed to soften and smooth the transitions between the images in the cine sequence, such as to prevent or reduce flicker, among other things. The workflow of a sonographer or other medical professional reviewing the real-time scan, however, typically includes navigating the real-time scan to analyze individual images within the cine sequence. The resolution and details of the individual images within the cine sequence are often poor because the image processing is optimized for viewing the real-time scan, as opposed to individual images within the real-time scan.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for enhancing the visualization of selected individual images from a real-time scan, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Figure 1:
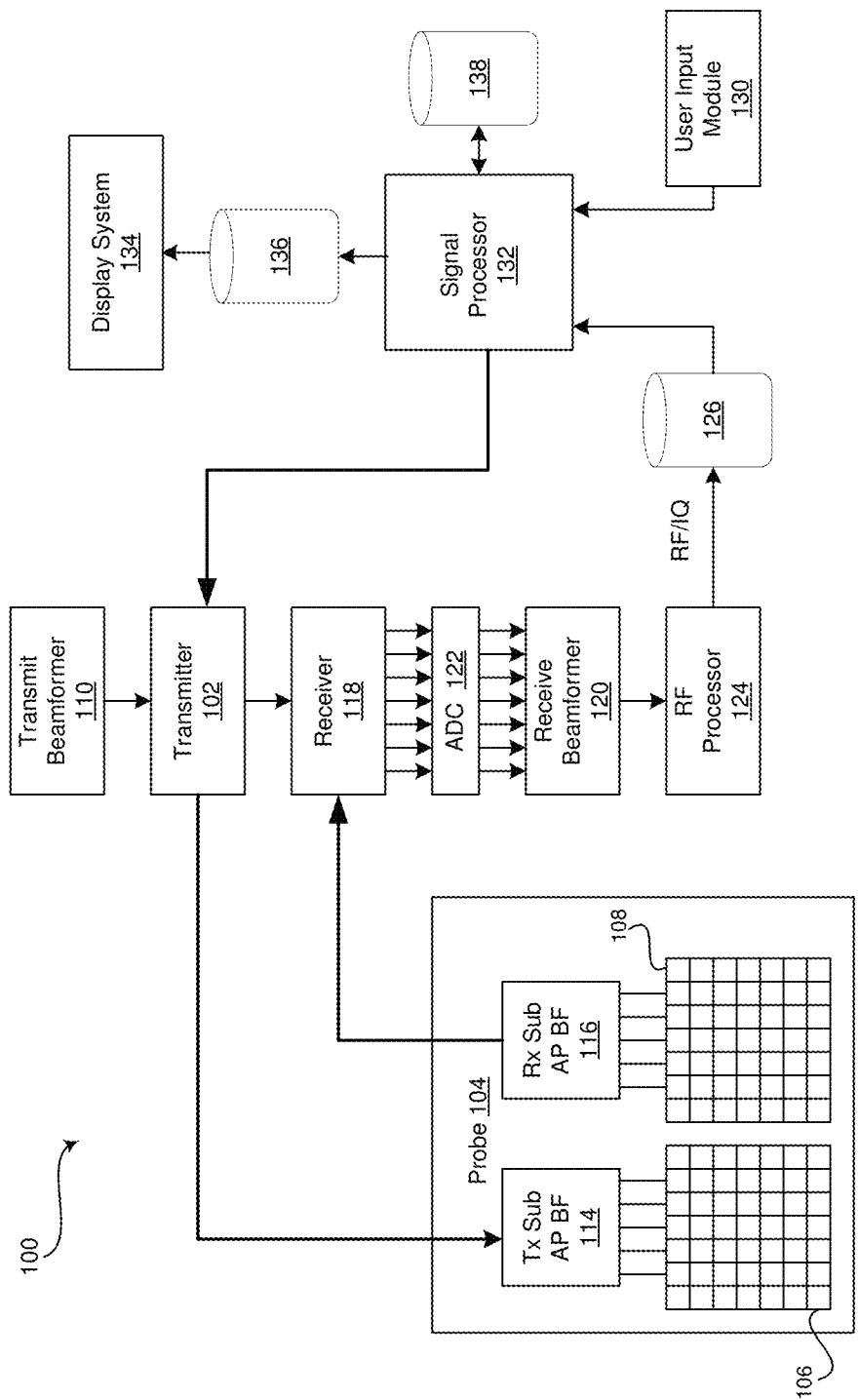
FIG. 1 is a block diagram of an exemplary ultrasound system that is operable to enhance visualization of selected individual images from a real-time scan, in accordance with an embodiment of the invention.

Certain embodiments of the invention may be found in a method and system for enhancing visualization of still images from a real-time ultrasound scan. For example, aspects of the present invention have the technical effect of enhancing the visualization of selected individual images from a real-time cine sequence by performing super-resolution image processing on raw ultrasound image data that corresponds with a frame of the cine sequence selected by activation of a trigger during review of the cine sequence. As another example, the technical effect of enhancing the visualization of selected individual images from a real-time scan may be realized by switching between first and second acquisition and processing modes based on a trigger. More specifically, the trigger may initiate a switch from acquiring, processing, and displaying a real-time image from a real-time scan at a first resolution based on primary acquisition imaging and processing parameters to acquiring, processing, and displaying a still image at a second resolution that is higher than the first resolution based on secondary acquisition imaging and processing parameters.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to enhance visualization of selected individual images from a real-time scan, in accordance with an embodiment of the invention. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a cine buffer 138, a signal processor 132, an image buffer 136, and a display system 134.

The transmitter 102 may comprise suitable logic, circuitry, interfaces and/or code that may be operable to drive an ultrasound probe 104. The ultrasound probe 104 may comprise a one dimensional (1D, 1.25D, 1.5D or 1.75D) array or a two dimensional (2D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108. The group of receive transducer elements 108 in the ultrasound probe 104 may be operable to convert the received echoes into analog signals, undergo sub-aperture beamforming by a receive sub-aperture beamformer 116 and are then communicated to a receiver 118.

The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122. The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, a scan mode, scan mode triggers, acquisition imaging parameters, acquisition processing parameters, settings, configuration parameters, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the cine buffer 138, the signal processor 132, the image buffer 136, and/or the display system 134.

In various embodiments, the user input module 130 may be operable to receive user input identifying acquisition imaging parameters for real-time scans and still image acquisitions. Imaging parameters, depending on the acquisition mode, may include a depth setting of an ultrasound image, a width setting of an ultrasound image, ultrasound image line density, a position of a region-of-interest (ROI), a pulse-repetition-frequency (PRF) setting of the ultrasound system 100, a gain setting of the ultrasound system 100, an adaptive gain setting of the ultrasound system 100, at least one transmit focus position of the ultrasound system 100, a position of a 3D acquisition region, or some combination.

The user input module 130 can be operable to receive user input identifying cine sequence processing parameters for a real-time scan and super-resolution processing parameters for a still image. Examples of processing parameters include a sampling rate, a dynamic range, persistence filter settings, gamma correction, and/or tissue filter settings, such as frame averaging, speckle reduction filtering, compounding, a number of compounding angles, and the like. The user input module 130 may be operable to receive user input identifying a trigger for selecting an image of a cine sequence, such that raw ultrasound image data corresponding with the selected individual image may be processed to generate a still image having a higher resolution than the frame in the cine sequence. The trigger may be, for example, an automatic trigger or a user trigger. An automatic trigger may be a condition detected during review of a cine sequence, such as pausing or stopping at a frame of the cine sequence, among other things. A user trigger may be a button or other control of the user input module 130 that is set-up to select a frame of a cine sequence for super-resolution processing or to switch from real-time acquisition imaging and processing parameters to still image acquisition imaging and processing parameters during an ultrasound scan. In a representative embodiment, the user input module 130 may be operable to navigate a cine sequence presented at a display system 134.

The signal processor 132 may comprise suitable logic, circuitry, interfaces and/or code that may be operable to process the ultrasound scan data for generating an ultrasound image for presentation on a display system 134. In an exemplary embodiment, the signal processor 132 may store the acquired raw ultrasound data in a cine buffer 138. The signal processor 132 is operable to perform one or more processing operations on the raw ultrasound data according to a plurality of selectable ultrasound modalities and acquisition processing parameters, such as cine sequence processing parameters or super-resolution still image processing parameters, for example. The ultrasound scan data may be processed in real-time during a scanning session as the echo signals are received. Additionally or alternatively, the ultrasound scan data stored in the cine buffer 138 and/or temporarily stored in the RF/IQ buffer 126 may be processed in less than real-time in a live or off-line operation.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include suitable logic, circuitry, interfaces and/or code that may be operable to process raw image data acquired by the ultrasound system 100 in multiple image acquisition imaging and/or processing modes. For example, based on user input received at the user input module 130, the signal processor 132 may be configured to process image data for a real-time cine sequence having corresponding imaging and/or processing parameters. The signal processor 132 may be configured to retrieve raw image data from the cine buffer 138 and process the image data for a still image having corresponding imaging and/or processing parameters in response to a trigger. The trigger may identify a frame of a cine sequence during review of a real-time scan or may identify a time during a real-time scan to switch from a real-time scan acquisition mode to a still image acquisition mode. The processed cine sequence and still image(s) may be displayed on the display system 134.

As defined herein, a real-time scan or cine sequence may be a 2D or 4D real-time motion imaging scan. A still image may include 2D and 3D images, for example. In various embodiments, super-resolution acquisition processing parameters may be used to process raw ultrasound image data to generate still images of higher quality than individual images within a cine sequence, where the cine sequence is processed according to cine sequence acquisition processing parameters. Processing parameters, depending on whether the processor 132 is generating a still image or a cine sequence, may include a selected or pre-defined sampling rate, a dynamic range setting, persistence filter settings, gamma correction settings, and/or tissue filter settings, such as frame averaging, speckle reduction filtering, compounding, a number of compounding angles, and the like. A trigger, such as an automatic trigger or a user trigger, may initiate super-resolution imaging processing to generate a still image. For example, an automatic trigger may be a condition detected by the signal processor 132 as a user navigates a cine sequence presented at display system 134, such as when a user input module 130 is used to pause or stop to view a frame of the cine sequence. A user trigger may be a button or other control of the user input module 130 that is set-up to activate super-resolution processing of raw ultrasound image data corresponding to, for example, a currently viewed frame of a cine sequence.

Figure 2:
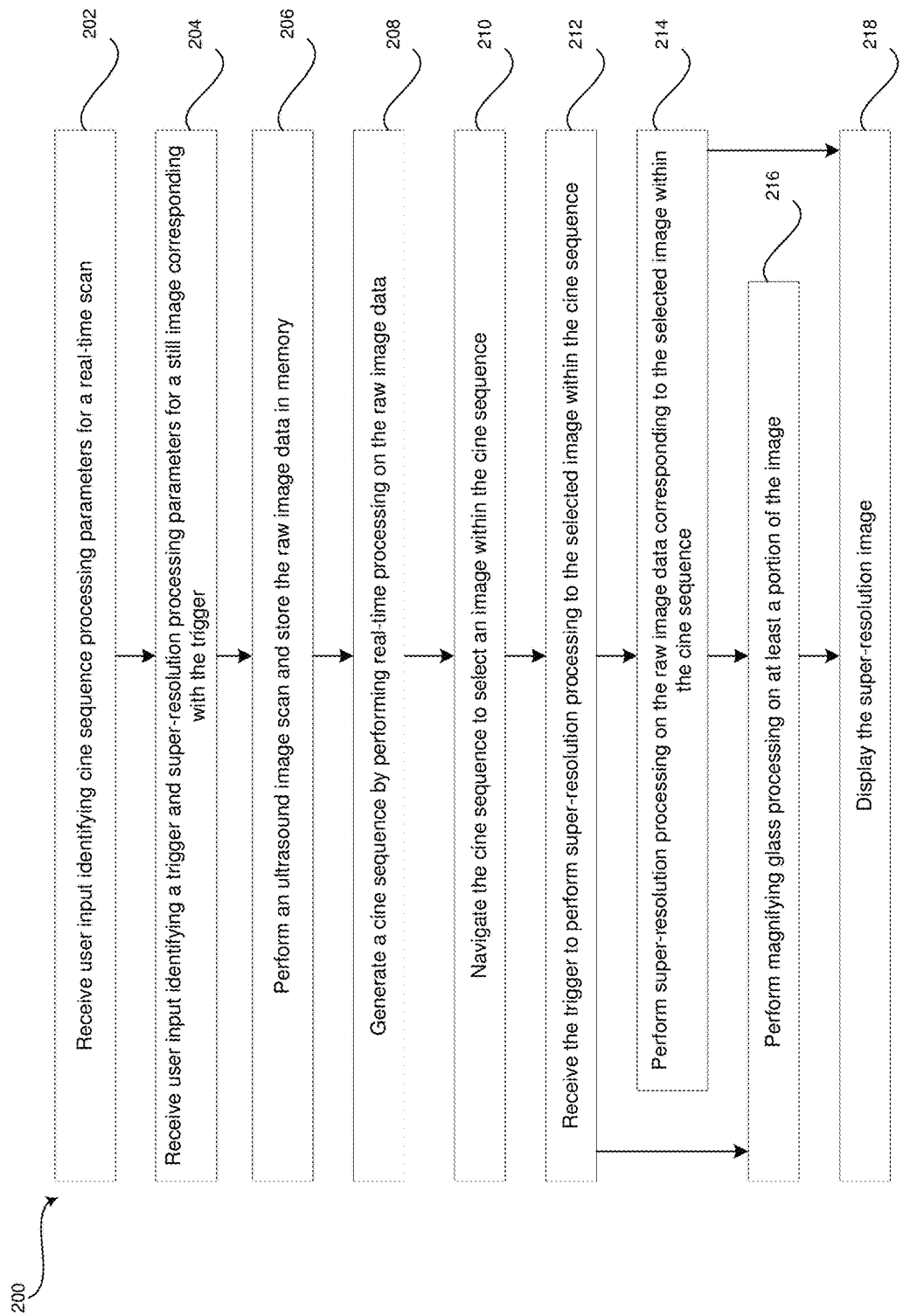
FIG. 2 is a flow chart illustrating exemplary steps that may be utilized for enhancing the visualization of selected individual images from a real-time scan, in accordance with an embodiment of the invention.
Figure 3:
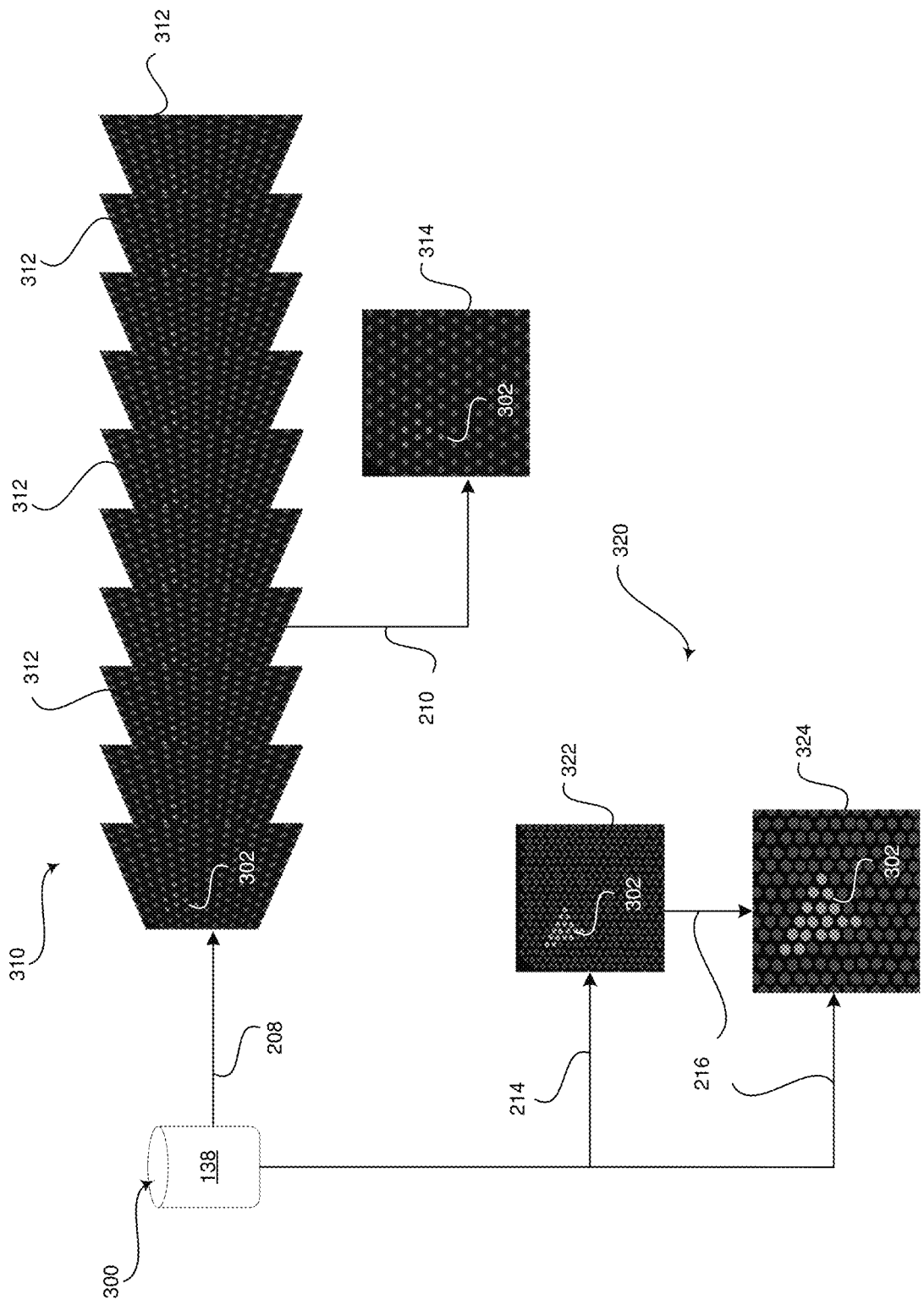
FIG. 3 is a diagram illustrating an exemplary process corresponding with flow chart steps of FIG. 2 that may be utilized for enhancing the visualization of selected individual images from a real-time scan, in accordance with an embodiment of the invention.

FIG. 2 is a flow chart 200 illustrating exemplary steps 202-218 that may be utilized for enhancing the visualization of selected individual images 312, 314 from a real-time scan 310, in accordance with an embodiment of the invention. FIG. 3 is a diagram illustrating an exemplary process corresponding with flow chart steps 208, 210, 214, 216 of FIG. 2 that may be utilized for enhancing the visualization of selected individual images 312, 314 from a real-time scan 310. Referring to FIG. 2, there is shown a flow chart 200 comprising exemplary steps 202 through 218. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 202, a user input may be received at the user input module 130 identifying cine sequence processing parameters for a real-time scan 310. The real-time scan 310 can be, for example, a 2D or 4D real-time motion imaging scan. The acquisition processing parameters may include, for example, a low sampling rate, a low dynamic range, a high persistence filter setting, and other processing settings optimized for real-time processing, such as tissue filter settings and gamma correction settings. The cine sequence acquisition processing parameters may be stored in association with the real-time scan mode and applied when processing raw ultrasound image data 300 for display as a cine sequence 310 at a display system 134. In various embodiments, one or more of the cine sequence acquisition processing parameters may be default parameters that may be optionally changed at the user input module 130.

In step 204, a user input may be received at the user input module 130 identifying super-resolution processing parameters for a still image 320 and a trigger for initiating the super-resolution processing performed by signal processor 132. The still image 320 may be, for example, a 2D or 3D static image. The super-resolution processing parameters can include, for example, a high sampling rate, a high dynamic range, a low persistence filter setting, and other processing settings optimized for static image processing. The super-resolution processing parameters generate still images 320 with higher resolution than individual images 312, 314 from the real-time scan 310 processed according to the cine sequence processing parameters. The trigger may be an automatic trigger, a user trigger, or any suitable trigger for selecting a frame 312, 314 in a cine sequence 310 and corresponding raw ultrasound image data 300 for processing by signal processor 132. The super-resolution processing parameters, such as the parameters discussed above, may be stored in association with the still image processing mode and applied when processing raw ultrasound image data 300 for display as a still image 320 at a display system 134. In an exemplary embodiment, one or more of the super-resolution processing parameters may be default parameters that may be optionally changed at the user input module 130.

In step 206, the ultrasound system 100 performs a scan. The raw ultrasound image data 300 acquired during the scan is stored in a cine buffer 138.

In step 208, the signal processor 132 generates a cine sequence 310 by performing real-time processing on the raw ultrasound image data 300 according to the cine sequence processing parameters. For example, as illustrated in FIG. 3, the signal processor 132 may retrieve raw ultrasound image data 300 from the cine buffer 138 and generate 208 a cine sequence 310 having a plurality of frames 312. The cine sequence processing parameters are defined to provide a smooth, soft, flicker-free playback of the cine sequence 310. The anatomical structure 302 shown in the individual frames 312 of the cine sequence 310, however, may be blurry or otherwise of poor quality when playback of a cine sequence 310 is stopped or paused to view an individual frame 312.

In step 210, user input may be received to navigate a cine sequence 310 presented at a display system 134. For example, instructions for playing back, rewinding, fast-forwarding, pausing, stopping, and the like may be received at a user input module 130 for reviewing and analyzing a real-time scan 310. As illustrated in FIG. 3, the frames 312 of the cine sequence 310 can be navigated to a selected one or more frames 314. The structure 302 shown in the selected frame(s) 314 may be difficult to view due to the poor resolution of individual frames 312, 314 of the cine sequence 310.

In step 212, the signal processor 132 receives a trigger to perform super-resolution processing of raw ultrasound data corresponding to the selected image 314 within the cine sequence 310. The trigger can be set-up at step 204 and may be, for example, an automatic trigger, a user trigger, or any suitable trigger. The automatic trigger may be a condition detected by the signal processor 132 as the cine sequence 310 presented at display system 134 is navigated at step 210. For example, an automatic trigger may be initiated when a user input module 130 is used to pause or stop to view a frame 314 of the cine sequence 310. The user trigger may be a button or other control of the user input module 130 that is set-up at step 204 to activate super-resolution processing of raw ultrasound image data corresponding to the frame 314 of the cine sequence 310 selected at step 210.

In step 214, the signal processor 132 performs super-resolution processing on the raw ultrasound data 300 that corresponds with the selected image 314 within the cine sequence 310. For example, as illustrated in FIG. 3, the signal processor 132 retrieves raw ultrasound image data 300 from the cine buffer 138 and generates 214 a still image 322 for presentation at display system 134 in step 218. The super-resolution processing parameters are defined to provide a high resolution still image 322. The anatomical structure 302 shown in the still image 322 is more readily identifiable because the signal processor 132 performing the super-resolution processing generates the still image 322 having a higher resolution than the corresponding selected frame 314 from the cine sequence 310.

In step 216, the signal processor 132 may perform magnifying glass processing on at least a portion of the raw ultrasound image data 300 and/or the super-resolution processed still image 322 to generate a magnified still image 324. As illustrated in FIG. 3, the magnifying glass processing may be in addition to or as an alternative to the super-resolution processing performed in step 214. The portion of the raw ultrasound image data 300 or the super-resolution processed still image 322 for magnification may be manually selected based on user input received at a user input module 130 or automatically selected based on image recognition techniques, a previously-selected region of interest, or any suitable automated selection. For example, the trigger defined at step 204 may specify the portion for magnification. The anatomical structure 302 shown in the magnified still image 324 is more readily identifiable because the signal processor 132 performing the magnifying glass processing generates the still image 324 having a magnified and/or higher pixel or voxel resolution than the corresponding selected frame 314 from the cine sequence 310.

In step 218, the higher resolution and/or magnified still image 320 generated in steps 214 and/or 216 is presented at display system 134. The still image 320 may be displayed separate from or in addition to the cine sequence 310. The resolution of the still image 320 is greater than the resolution of the individual images 312, 314 of the cine sequence 310. The activation of the trigger, therefore, provides enhanced visualization of structure 302 presented in the selected frame 314 of the cine sequence 310 by initiating the processing and display of the corresponding still image 320.

Figure 4:
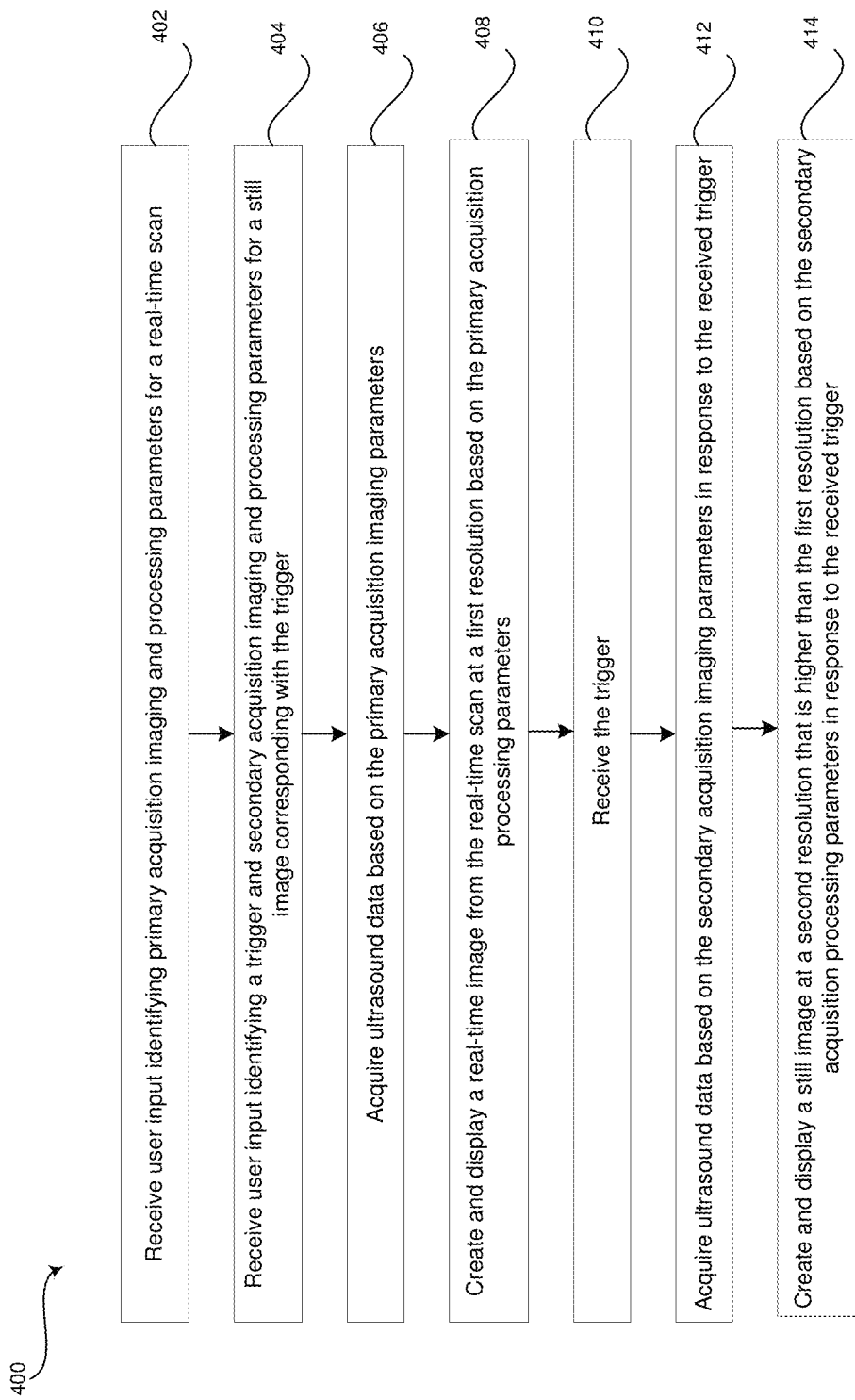
FIG. 4 is a flow chart illustrating exemplary steps that may be utilized for displaying a real-time scan at a first resolution based on first acquisition and processing parameters and, in response to a trigger, displaying a still image at a second resolution that is higher than a first resolution based on second acquisition and processing parameters, in accordance with an embodiment of the invention.

FIG. 4 is a flow chart illustrating exemplary steps that may be utilized for displaying a real-time scan 310 at a first resolution based on first acquisition and processing parameters and, in response to a trigger, displaying a still image 320 at a second resolution that is higher than a first resolution based on second acquisition and processing parameters, in accordance with an embodiment of the invention. Referring to FIG. 4, there is shown a flow chart 400 comprising exemplary steps 402 through 414. Certain embodiments of the present invention may omit one or more of the steps, and/or perform the steps in a different order than the order listed, and/or combine certain of the steps discussed below.

For example, some steps may not be performed in certain embodiments of the present invention. As a further example, certain steps may be performed in a different temporal order, including simultaneously, than listed below.

In step 402, a user input may be received at the user input module 130 identifying primary acquisition imaging and processing parameters for a real-time scan. The real-time scan can be, for example, a 2D or 4D real-time motion imaging scan. The acquisition imaging parameters may include various settings for depth, width, line density, position of a region-of-interest (ROI), pulse-repetition-frequency (PRF), gain, adaptive gain, transmit focus position, or some combination of settings optimized for a real-time scan. The acquisition processing parameters may include, for example, a low sampling rate, a low dynamic range, a high persistence filter setting, and other processing settings optimized for real-time processing. The real-time acquisition imaging and processing parameters may be stored in association with the real-time scan mode and applied when acquiring and processing real-time image data for display as a cine sequence 310 at a display system 134. In various embodiments, one or more of the real-time acquisition imaging and processing parameters may be default parameters that may be optionally changed at the user input module 130.

In step 404, a user input may be received at the user input module 130 identifying secondary acquisition imaging and processing parameters for a still image 320 and a trigger for initiating the still image acquisition and processing performed by ultrasound system 100. The still image 320 may be, for example, a 2D or 3D static image. The acquisition imaging parameters may include various settings for depth, width, line density, position of a region-of-interest (ROI), pulse-repetition-frequency (PRF), gain, adaptive gain, transmit focus position, or some combination of settings optimized for a still image acquisition. The acquisition processing parameters may include, for example, a high sampling rate, a high dynamic range, a low persistence filter setting, and other processing settings optimized for static image processing. The still image acquisition imaging and processing parameters generate still images 320 with higher resolution than individual images 312, 314 from the real-time scan 310 acquired and processed according to the real-time acquisition imaging and processing parameters. The trigger may be a timer trigger, an automatic trigger, a user trigger, or any suitable trigger for switching from primary acquisition imaging and processing parameters to secondary acquisition imaging and processing parameters. The trigger and the secondary acquisition imaging and processing parameters may be stored in association with the still image processing mode and applied when the trigger is received to acquire and process image data for display as a still image 320 at a display system 134. In an exemplary embodiment, one or more of the secondary acquisition imaging and processing parameters may be default parameters that may be optionally changed at the user input module 130.

In step 406, the ultrasound system 100 acquires image data based on the primary acquisition imaging parameters. The ultrasound system 100 acquires the real-time image data using the stored primary acquisition imaging parameters that can be default parameters and/or parameters obtained at step 402 above. The image data acquired by the ultrasound system 100 may be stored at a cine buffer 138. In step 408, the signal processor 132 processes the image data acquired at step 406 to create a cine sequence 310 based on the primary acquisition processing parameters. The cine sequence 310 comprises a plurality of images 312, each having a first resolution. The cine sequence 310 is presented at a display system 134.

In step 410, the ultrasound system 100 receives a trigger to switch from the primary acquisition imaging and processing parameters to the secondary acquisition imaging and processing parameters. The trigger can be set-up at step 404 and may be, for example, a timer trigger, an automatic trigger, a user trigger, or any suitable trigger. The timer trigger may switch from primary image acquisition imaging and processing parameters to secondary acquisition imaging and processing parameters at a predetermined interval that can be set-up at step 404. The automatic trigger may include switching from the primary acquisition imaging and processing parameters to the secondary acquisition imaging and processing parameters when one or more conditions of the ultrasound system 100 have been satisfied, such as when a condition is detected in the acquired ultrasound image data, among other things. The user trigger can be a button, switch, or any suitable mechanism that may be activated by a user to initiate the secondary acquisition imaging and processing parameters.

In step 412, the ultrasound system 100 acquires image data based on the secondary acquisition imaging parameters in response to the received trigger. The ultrasound system 100 acquires the still image data using the stored secondary acquisition imaging parameters that can be default parameters and/or parameters obtained at step 404 above. The image data acquired by the ultrasound system 100 may be stored at a cine buffer 138. In step 414, the signal processor 132 processes the image data acquired at step 412 to create a still image 320 based on the secondary acquisition processing parameters. The still image 320 can be a magnified image 324 and/or a high resolution image 322. The still image 320 is presented at a display system 134 separate from and/or in addition to the real-time scan 310 displayed at step 408. The still image 320 is processed and displayed at a second resolution that is greater than the first resolution of the individual images 312, 314 of the cine sequence 310.

Aspects of the present invention provide a system 100 and method 200, 400 for enhancing the visualization of selected individual images 312, 314 from a real-time scan 310. In accordance with various embodiments of the invention, a method 200, 400 comprises acquiring 206, 406, 412 ultrasound image data 300 at an ultrasound system 100. The method 200, 400 comprises processing 208, 408 the acquired ultrasound image data 300, by a processor 132, according to cine sequence processing parameters to generate a cine sequence 310. The cine sequence 310 comprises a plurality of frames 312, 314, each having a first resolution. The method 200, 400 comprises receiving a trigger 212, 410 at the processor 132. The method 200, 400 comprises processing 214, 216 the acquired ultrasound image data 300, by the processor 132, according to still image processing parameters in response to the trigger to generate a still image 320 having a second resolution that is higher than the first resolution.

In a representative embodiment, the method 200, 400 comprises receiving 202, 402 user input at a user input module 130 identifying one or more of the cine sequence processing parameters and cine sequence imaging parameters prior to acquiring 206, 406, 412 the ultrasound image data 300. In various embodiments, the method 200, 400 comprises receiving 204, 404 user input at a user input module 130 identifying one or more of the still image processing parameters, still image imaging parameters, and the trigger prior to acquiring 206, 406, 412 the ultrasound image data and receiving 212, 410 the trigger.

In certain embodiments, the method 200 comprises storing 206 the acquired ultrasound image data in memory 138. The method 200 comprises navigating 210, in response to instructions received at a user input module 130, the cine sequence 310 to one 314 of the plurality of frames 312. The received trigger selects the one 314 of the plurality of frames 312. The method 200 comprises retrieving 214, by the processor 132, a portion of the acquired ultrasound image data 300 from the memory 138 that corresponds with the one 314 of the plurality of frames 312 selected by the trigger. The method 200 comprises processing 214 the portion of the acquired ultrasound image data 300, by the processor 132, to generate the still image 322. In various embodiments, the method 200 comprises processing 216 at least a portion of the still image 322, by the processor 132, according to magnifying glass processing parameters to generate a magnified still image 324. In a representative embodiment, the trigger comprises an automatic trigger configured to activate when the cine sequence 310 is navigated to the one 314 of the plurality of frames 312 by one or more of pausing or stopping the cine sequence 310 at the one 314 of the plurality of frames 312. Additionally or alternatively, the trigger comprises a user trigger configured to activate based on an input received at a user input module 130.

In various embodiments, the acquired ultrasound image data 300 processed to generate the cine sequence 310 is acquired based on cine sequence imaging parameters. The acquired ultrasound image data 300 processed to generate the still image 320 is acquired based on still image imaging parameters. In certain embodiments, the trigger comprises one or more of a timer trigger configured to activate at one or more predetermined times, an automatic trigger configured to activate when at least one condition is detected in the acquired ultrasound image data, and a user trigger configured to activate based on an input received at a user input module 130. In a representative embodiment, the cine sequence 310 is one of a two-dimensional (2D) real-time motion imaging scan and a four-dimensional (4D) imaging scan. The still image 320 is one of a static two-dimensional (2D) imaging acquisition and a static three-dimensional (3D) imaging acquisition.

In accordance with various embodiments of the invention, a system comprises an ultrasound device 100 operable to acquire ultrasound image data 300. The system comprises a processor 132 operable to process the acquired ultrasound image data 300 according to cine sequence processing parameters to generate a cine sequence 310. The cine sequence 310 comprises a plurality of frames 312, 314, each having a first resolution. The processor 132 is operable to receive a trigger. The processor 132 is operable to process the acquired ultrasound image data 300 according to still image processing parameters in response to the received trigger to generate a still image 320 having a second resolution that is higher than the first resolution.

In a representative embodiment, the system comprises a user input module 130 configured to receive user input identifying one or more of the cine sequence processing parameters and cine sequence imaging parameters prior to acquiring the ultrasound image data 300. The user input module 130 is additionally or alternatively configured to receive user input identifying one or more of the still image processing parameters, still image imaging parameters, and the trigger prior to acquiring the ultrasound image data 300 and receiving the trigger. Additionally or alternatively, the user input module 130 is configured to receive user input provided as the trigger to either (1) select one 314 of the plurality of frames 312 of the cine sequence 310 that corresponds with a portion of the acquired ultrasound image data 300 that is processed to generate the still image 320, or (2) switch from acquiring ultrasound image data according to the cine sequence imaging parameters and processing the acquired ultrasound image data according to the cine sequence processing parameters to acquiring ultrasound image data according to the still image imaging parameters and processing the acquired ultrasound image data according to the still image processing parameters.

In certain embodiments, the system comprises a memory 138 configured to store the acquired ultrasound image data 300. The system comprises a user input module 130 configured to receive instructions for navigating the cine sequence 310 to one 314 of the plurality of frames 312. The received trigger selects the one 314 of the plurality of frames 312. The processor 132 is configured to retrieve a portion of the acquired ultrasound image data 300 from the memory 138 that corresponds with the one 314 of the plurality of frames 312 selected by the trigger and process the portion of the acquired ultrasound image data 300 to generate the still image 322.

In various embodiments, the processor 132 is configured to process at least a portion of the still image 322 according to magnifying glass processing parameters to generate a magnified still image 324. In a representative embodiment, the trigger comprises an automatic trigger configured to activate when the cine sequence 310 is navigated to the one 314 of the plurality of frames 312 by one or more of pausing or stopping the cine sequence 310 at the one 314 of the plurality of frames 312. Additionally or alternatively, the trigger comprises a user trigger configured to activate based on an input received at a user input module 130. In certain embodiments, the acquired ultrasound image data 300 processed to generate the cine sequence 310 is acquired by the ultrasound device 100 based on cine sequence imaging parameters. The acquired ultrasound image data 300 processed to generate the still image 320 is acquired by the ultrasound device 100 based on still image imaging parameters.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhancing the visualization of selected individual images from a real-time scan.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
   acquiring ultrasound image data at an ultrasound system;
   storing the acquired ultrasound image data in memory;
   processing the acquired ultrasound image data, by a processor, according to cine sequence processing parameters to generate a cine sequence comprising a plurality of frames, wherein each of the frames has a first spatial resolution;
   navigating, in response to instructions received at a user input module, the cine sequence to one of the plurality of frames;
   receiving a trigger at the processor, wherein the received trigger selects the one of the plurality of frames;
   retrieving, by the processor, a portion of the acquired ultrasound image data from the memory that corresponds with the one of the plurality of frames selected by the trigger; and
   processing the portion of the acquired ultrasound image data, by the processor, according to still image processing parameters in response to the trigger to generate a still image having a second spatial resolution that is higher than the first spatial resolution.

2. The method according to claim 1, comprising receiving user input at a user input module identifying the cine sequence processing parameters prior to acquiring the ultrasound image data.

3. The method according to claim 1, comprising receiving user input at a user input module identifying one or more of the still image processing parameters and the trigger prior to acquiring the ultrasound image data and receiving the trigger.

4. The method according to claim 1, comprising processing at least a portion of the still image, by the processor, according to magnifying glass processing parameters to generate a magnified still image.

5. The method according to claim 1, wherein the trigger comprises one or more of:
   an automatic trigger configured to activate when the cine sequence is navigated to the one of the plurality of frames by one or more of pausing or stopping the cine sequence at the one of the plurality of frames, and
   a user trigger configured to activate based on an input received at a user input module.

6. The method according to claim 1, wherein the cine sequence is one of:
   a two-dimensional (2D) real-time motion imaging scan, and
   a four-dimensional (4D) imaging scan; and
   wherein the still image is one of:
   a static two-dimensional (2D) imaging acquisition, and
   a static three-dimensional (3D) imaging acquisition.

7. A system, comprising:
   an ultrasound device operable to acquire ultrasound image data;
   a memory configured to store the acquired ultrasound image data;
   a processor operable to:
     process the acquired ultrasound image data according to cine sequence processing parameters to generate a cine sequence comprising a plurality of frames, wherein each of the frames has a first spatial resolution, and
     receive a trigger; and
   a user input module configured to receive instructions for navigating the cine sequence to one of the plurality of frames, wherein the received trigger selects the one of the plurality of frames,
   wherein the processor is configured to:
     retrieve a portion of the acquired ultrasound image data from the memory that corresponds with the one of the plurality of frames selected by the trigger, and
     process the portion of the acquired ultrasound image data according to still image processing parameters in response to the received trigger to generate a still image having a second spatial resolution that is higher than the first spatial resolution.

8. The system according to claim 7, comprising a user input module configured to receive one or more of:
   user input identifying the cine sequence processing parameters prior to acquiring the ultrasound image data,
   user input identifying one or more of the still image processing parameters and the trigger prior to acquiring the ultrasound image data and receiving the trigger, and
   user input provided as the trigger to select one of the plurality of frames of the cine sequence that corresponds with a portion of the acquired ultrasound image data that is processed to generate the still image.

9. The system according to claim 7, wherein the processor is configured to process at least a portion of the still image according to magnifying glass processing parameters to generate a magnified still image.

10. The system according to claim 7, wherein the trigger comprises one or more of:
    an automatic trigger configured to activate when the cine sequence is navigated to the one of the plurality of frames by one or more of pausing or stopping the cine sequence at the one of the plurality of frames, and
    a user trigger configured to activate based on an input received at a user input module.

11. A non-transitory computer readable medium having stored thereon, a computer program having at least one code section, the at least one code section being executable by a machine for causing the machine to perform steps comprising:
    acquiring ultrasound image data;
    storing the acquired ultrasound image data in memory;
    processing the acquired ultrasound image data according to cine sequence processing parameters to generate a cine sequence comprising a plurality of frames, each of the frames having a first spatial resolution;
    navigating the cine sequence to one of the plurality of frames;
    receiving a trigger, wherein the received trigger selects the one of the plurality of frames;
    retrieving a portion of the acquired ultrasound image data from the memory that corresponds with the one of the plurality of frames selected by the trigger; and
    processing the portion of the acquired ultrasound image data according to still image processing parameters in response to the trigger to generate a still image having a second spatial resolution that is higher than the first spatial resolution.

12. The non-transitory computer readable medium according to claim 11, comprising receiving one or more of:
    user input identifying the cine sequence processing parameters prior to acquiring the ultrasound image data, and
    user input identifying one or more of the still image processing parameters and the trigger prior to acquiring the ultrasound image data and receiving the trigger.

13. The non-transitory computer readable medium according to claim 11, comprising processing at least a portion of the still image according to magnifying glass processing parameters to generate a magnified still image.

* * * * *